United States Patent [19]

Geren

[11] Patent Number: 4,457,221

[45] Date of Patent: Jul. 3, 1984

[54] STERILIZATION APPARATUS

[76] Inventor: David K. Geren, 4601 Gloria Ave., Encino, Calif. 91436

[21] Appl. No.: 525,991

[22] Filed: Aug. 8, 1983

Related U.S. Application Data

[63] Continuation-in-part of Ser. No. 219,459, Dec. 23, 1980, abandoned.

[51] Int. Cl.³ .......................... A23L 3/00; A23L 3/26; A23L 3/32
[52] U.S. Cl. .......................... 99/451; 99/516; 99/536; 204/194; 204/DIG. 8; 210/748; 219/284; 422/23; 426/238; 426/244
[58] Field of Search ................. 219/284–295; 99/451, 483, 467, 468, 485, 486, 516, 534, 535, 536, 646 R; 426/244, 246, 234–238, 247; 210/748; 204/165, 194, 302, DIG. 8; 422/22, 23, 95

[56] References Cited

U.S. PATENT DOCUMENTS

| | | | |
|---|---|---|---|
| 535,267 | 3/1895 | Wagner | 219/291 X |
| 645,569 | 3/1900 | Roberts | 99/451 |
| 930,772 | 8/1909 | Lincoln | 99/451 |
| 1,360,447 | 11/1920 | Rudd | 99/451 |
| 1,934,703 | 11/1933 | Golden | |
| 1,975,805 | 10/1934 | Smith | |
| 2,081,243 | 5/1937 | Macy | |
| 2,324,837 | 7/1943 | Hall | 219/291 |
| 2,569,075 | 9/1951 | Schade | 426/244 |
| 3,753,886 | 8/1973 | Myers | 210/748 |
| 3,933,606 | 1/1976 | Harms | 210/748 |

FOREIGN PATENT DOCUMENTS

| | | | |
|---|---|---|---|
| 7307056 | 11/1974 | Netherlands | 210/748 |
| 667362 | 2/1952 | United Kingdom | 426/244 |

*Primary Examiner*—Timothy F. Simone
*Attorney, Agent, or Firm*—Harry R. Lubcke

[57] ABSTRACT

A process and apparatus for killing organisms in situ within a host by means of successive short-duration high-current-density pulses of electricity of alternately opposite polarity. These pulses are passed through the host and concomitantly the organisms for a period of a few seconds. The cellular structure of the host is not destroyed, nor is the temperature thereof appreciably elevated. The current is conveyed to the host from electrodes immersed with the host in a weak electrolyte. The pulses are formed by phase-controlled thyristors.

12 Claims, 11 Drawing Figures

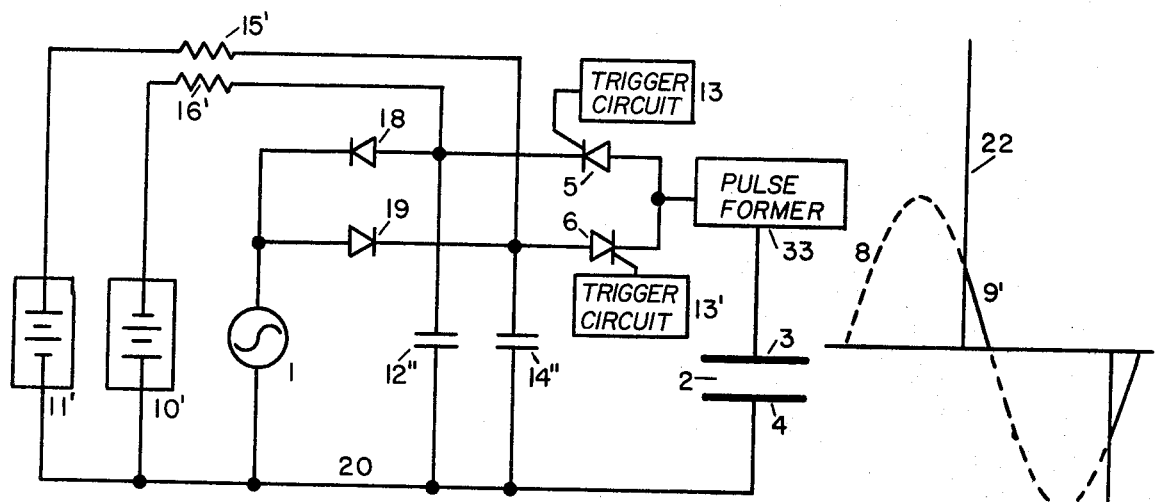
FIG. 7
FIG. 8
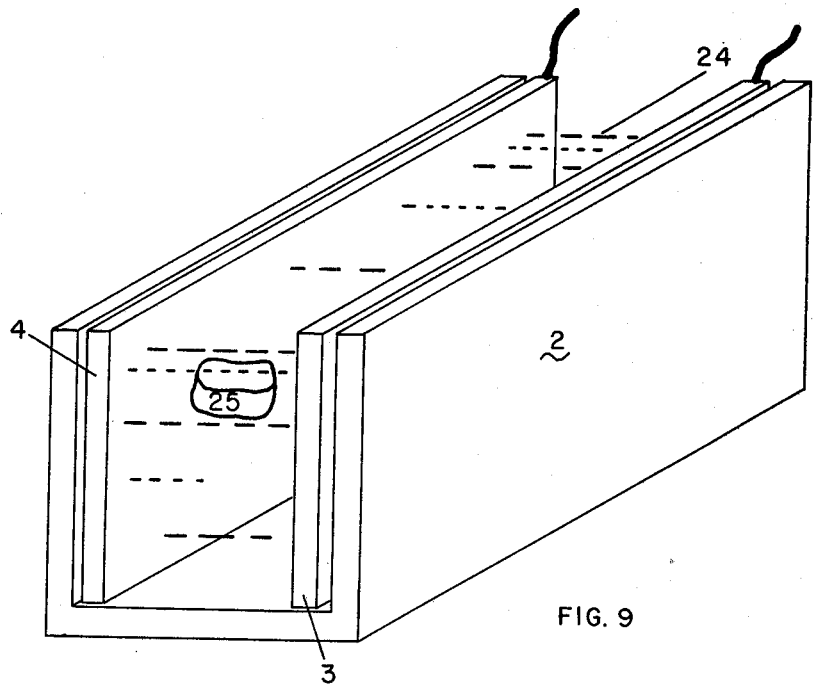
FIG. 9

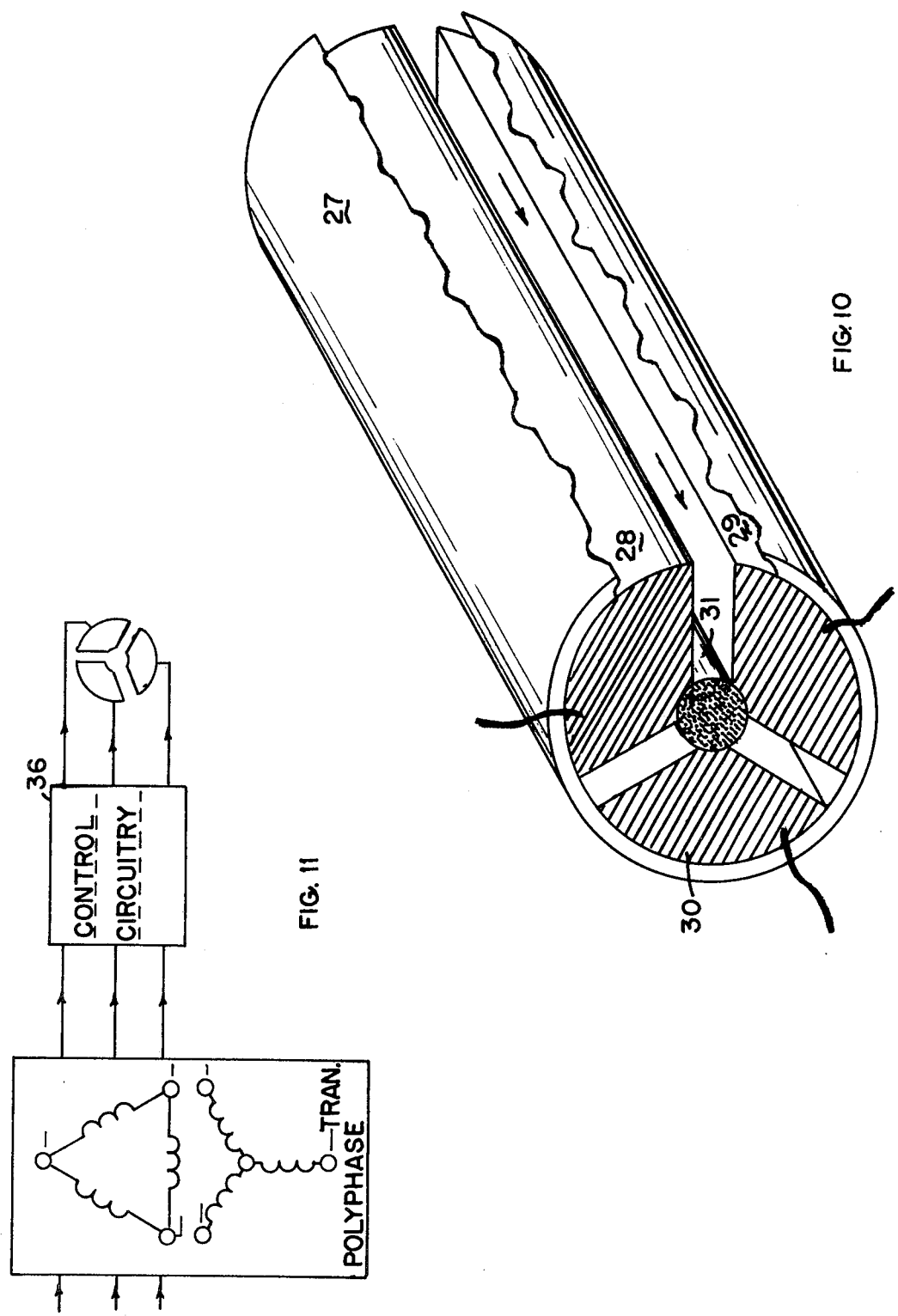

STERILIZATION APPARATUS

This is a continuation-in-part of application Ser. No. 06/219,459 filed Dec. 23, 1980, now abandoned.

BACKGROUND OF THE INVENTION

This invention pertains to a process and an apparatus for sterilizing by killing bacteria and similar organisms within a host. The host may be either a solid or a liquid.

Macy, U.S. Pat. No. 2,081,243, discloses apparatus for pasteurizing liquids only, such as milk, by "slow and intensive impulses of alternating electric current." These he produces by an interrupter at 3.33 times per second; the "interruptions literally exploding the bacteria." The temperature of the milk may also appreciably be raised by the process. The apparatus is of the coaxial flow-through type, having numerous parts.

Golden, U.S. Pat. No. 1,934,703, discloses a trough-like electrical sterilizing apparatus, having an internal central electrode and a pair of external flux-concentrator electrodes.

Smith, U.S. Pat. No. 1,975,805, discloses a dry type sterilizing apparatus, in which a high voltage upon a pair of rotating electrodes, coaxially spaced on opposite sides of a conveyor that carries the material to be sterilized, act upon the material.

SUMMARY OF THE INVENTION

A host, or a plurality of hosts, containing organisms to be killed are surrounded by a weak electrolyte within the influence of plural electrodes.

Successive high-density current pulses of alternating polarity, are caused to occur between 100 and 1,000 times per second, each having a typical duration of about 10% of each one-half cycle. These pulses are characterized by extremely high dI/dt initially and, in all but one embodiment, a succeeding lower level current flow of short duration.

The orgainsims are electrocuted by the passage of electric current through the host and concomitantly through the organisms. Bacteria are not "exploded" as observed by Macy. The explosive mode of destruction of the prior art likewise destroys the cell structure of the host substance, reducing its quality.

The current pulses are formed by electronic switches, suited to give a rapid rise of electric current, such as phase-controlled silicon controlled rectifiers (SCRs). Said electronic switches are referred to herein as "thryristors" and include any suitable electronic switching device.

BRIEF DESCRIPTION OF DRAWINGS

FIG. 7 is a diagram of a circuit combining the circuits of FIGS. 3 and 5.

FIG. 8 is the waveform for the circuit of FIG. 7. The time scale is not to scale.

FIG. 9 is a perspective view of a single-phase apparatus for processing according to this invention.

FIG. 10 is the same view for a three-phase apparatus.

FIG. 11 is a three-phase schematic circuit.

DETAILED DESCRIPTION OF THE PREFERRED EMBODIMENTS

Figure 1:
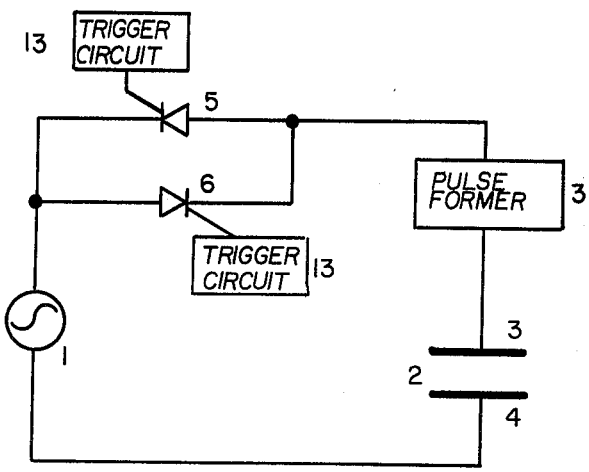
FIG. 1 is a schematic electical diagram of a single-phase alternating-current powered apparatus for accomplishing processing according to this invention.
Figure 5:
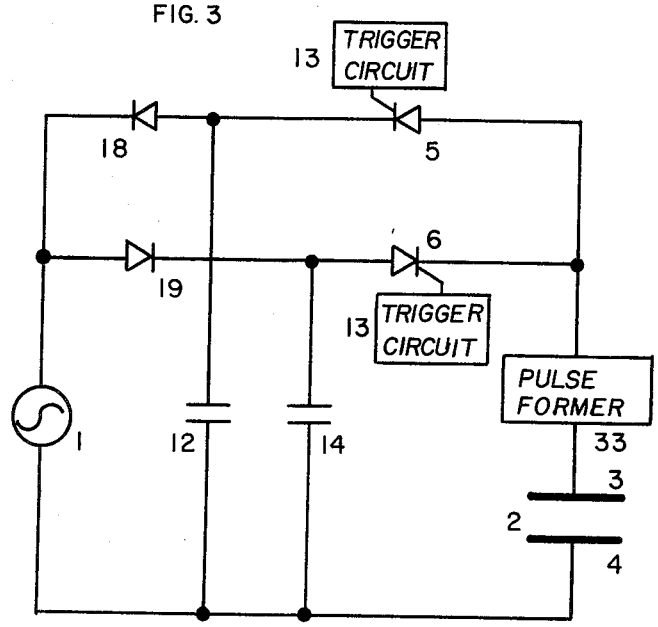
FIG. 5 is a schematic diagram of a circuit similar to that of FIG. 1, but including a pair of capacitors.

In FIGS. 1, 5 and 7 numeral 1 indicates a source of alternating and preferably sinusoidal current. For efficient and effective use of this invention the potential of this power source must be a minimum of approximately 100 volts rms. Voltages as high as 1,000 volts rms are practical also. The voltage utilized is a function of the nature of the material being treated, the conductivity of the electrolyte (in FIG. 9 see numeral 24), and the degree of effect desired in the particular application. For most media, a minimum practical potential is about 200 volts rms. Extremely delicate materials such as sea urchin roe (Japanese "uni") for example are best treated at a rms voltage from power source numeral 1 of between 100 and 150 volts rms.

In the embodiments of FIGS. 1, 5 and 7, significant bactericidal effects are obtained when the current density through the media being treated (be it solid or liquid) is 50 milliamperes (ma) per square centimeter (cross-sectional area) or more. Current densities as great as 5 amperes/$cm^2$ have been used with success.

In practice a current density ranging between 500 ma/$cm^2$ rms and 1.25 ampere/$cm^2$ is satisfactory for most media resulting in total treatment times of no more than several seconds. Electrode spacing and electrolyte conductivity should be adjusted to obtain a nominal conduction angle of 18 degrees (i.e. current flows 10% of the 180 degree one-half wave from power source numeral 1). Under no circumstance should the conduction angle be allowed to approach 90 degrees. Conduction angles permitting current flow for less than 200 microseconds in the embodiments of FIGS. 1, 5 and 7 are of reduced effectiveness.

Treatment cell 2 has parallel spaced electrodes 3 and 4. These are connected to power source 1 through oppositely poled phase-controlled electronic switches (thyristors) such as Silicon Controlled Rectifiers (SCRs), 5 and 6.

Figure 2:
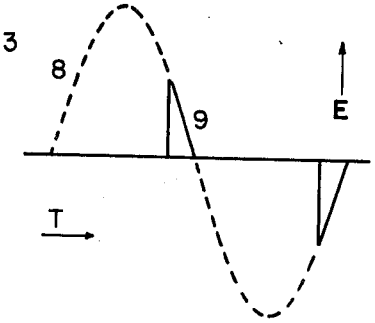
FIG. 2 is a current vs. time waveform that illustrates the operation of the circuit of FIG. 1. The time scale is not to scale for sake of clarity.

In FIG. 2, dotted sinusoidal wave 8 represents a cycle of voltage of source 1. Solid line spike 9 represents current. The current is limited to a brief interval of time, typically 10% of each half-wave cycle.

Hence, the minimum pulse width will be 200 microseconds. The maximum pulse width will be 5 milliseconds, occuring when current pulses alternate 100 times per second (power source frequency being 50 Hz).

FIG. 2 is not to true time scale, for sake of clarity.

It is desirable that the type of thyrister chosen be capable of very rapid turn-on. A steep turn-on wavefront is most effective in killing unwanted organisms within the host substance. Hence, a pulse forming network similar to that used for laser flash tube power supply networks (33) is desirable to obtain the necessary dI/dt required for great effectiveness and low power dissipation in the media being treated.

Figure 3:
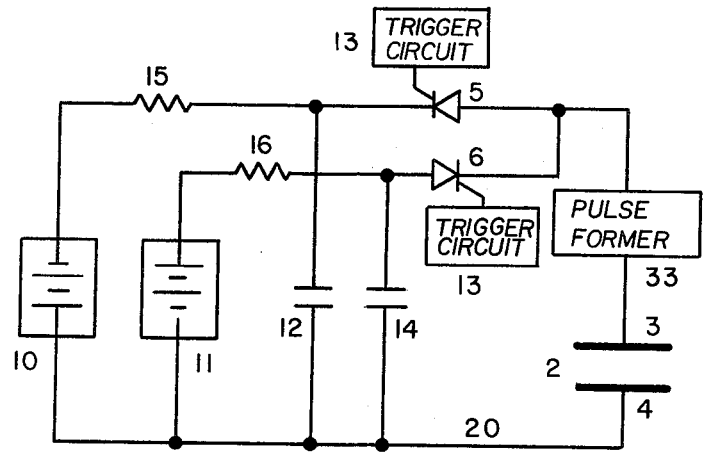
FIG. 3 is a schematic electrical diagram of a dual power-supply powered apparatus.

In FIG. 3, elements 2, 3, 4, 5 and 6 are the same as in FIG. 1. However, power source 1 is supplanted by relatively high voltage power supplies 10 and 11. These supplies provide direct current and charge capacitors 12 and 14 through resistors 15 and 16. The time constants of these resistor-capacitor combinations are roughly equal and are such as to allow a full charge of the capacitors fifty of more times per second, i.e. each cycle. The capacitors are of equal capacitance.

It is desirable that the rise time of the current spike that is obtained by the discharge of the capacitors (one at a time) be extremely rapid. Thus, the inductance of the capacitor, rectifier and treatment cell should be a minimum. This is enhanced by employing low inductance capacitors and a pulse forming network. A capacitance of 100 microfarads for each capacitor is suitable. Power supplies 10 and 11 must be of equal potential and at least 300 volts. d.c. for significant results.

Pulse-forming network 33 is placed in series with treatment cell 2 to increase the rate of change of current rise, i.e. dI/dt, thereby obtaining enhanced results.

Network 33 is especially effective where there are air bubbles or insulating material within the host. These are capacitive regions. By increasing the dI/dt, Fourier analysis of the wavefront shows that there is generally greater energy coupling at the higher frequencies. This results in good current conduction through the dielectric of the capacitive regions.

Operating voltages of one thousand volts or more may be produced by power supplies 10 and 11. Note that these are connected to the capacitors in opposite polarity.

Figure 4:
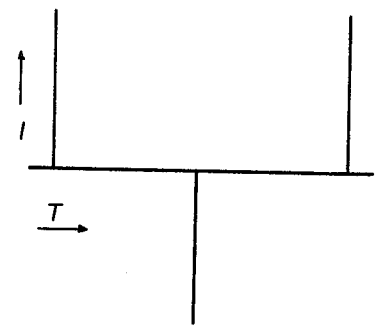
FIG. 4 is a current vs. time waveform for the circuit of FIG. 3. The time scale is not to scale for sake of clarity.

FIG. 4 shows the current waveform as a function of time. It is to be noted that the current spikes are extremely sharp and of brief duration. Pulse widths of 500 nanoseconds are obtainable. Hence, in practical applications of this invention it is feasible to obtain peak powers of $1 \times 10^7$ watts without suffering substantial temperature increases.

Alternating current pulses are utilized according to this invention to prevent polarization and plate-out effects in cell 2. Thus, both net positive and negative current flows are equal.

FIG. 5 shows the circuit for an improved modification of FIG. 1. Elements 1 through 6 are the same or similar to the same numbered elements in FIG. 1. Elements 12' and 14' are the same or similar to elements 12 and 14 in FIG. 3.

Figure 6:
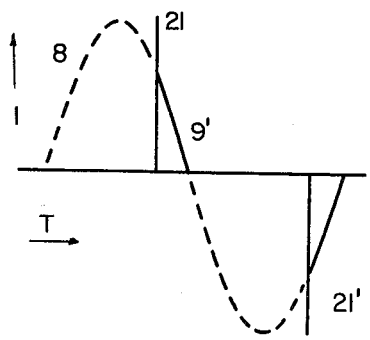
FIG. 6 is the waveform for the circuit of FIG. 5; not to time scale.

New element 18 is a diode, typically solid-state, that ceases to conduct at the maximum value of voltage waveshape 8 in FIG. 6. The peak voltage charge is thus retained on capacitor 12' and the current spike 21 at discharge is proportional to the peak voltage of waveshape 8. The current continues at reduced amplitude 9', as in FIGS. 1 and 2.

Diode 19 performs in the same manner with respect to capacitor 14', but in the opposite polarity, forming current spike 21'.

FIG. 7 combines the circuits of FIGS. 3 and 5. Analogous to those circuits, high amplitude current spikes 22 and 22' of opposite polarity are formed, as seen in FIG. 8. The reduced current 9' is also present.

A common return 20 is provided in FIG. 7. As before, the use of power supplies 10' and 11' allows current spikes of relatively great amplitude to be produced. Again, a pulse-forming network 33 may be placed in series with the treatment cell to increase the value of dI/dt. These networks utilize inductors and capacitors and are well known in the art of laser flash tube power supplies.

FIG. 9 illustrates in perspective a basic single-phase treatment cell 2. The shape is that of a hollow rectangular parallelopiped. In the figure the two ends are in phantom, so that the interior can be seen. In order to assure uniform current flow at all points between the electrodes (3 and 4), the electrodes must be of equal surface area, parallel and equidistant at all points in contact with the electrolyte (24).

Electrodes 3 and 4 are the same as those schematically shown in the earlier schematic circuit diagrams. The electrodes are normally simply affixed to the adjacent inner surface of the parallelopiped sides. However, these may be moved closer together when the internal electrical resistance of the cell is high.

An electrolyte 24 fills cell 2. For solid host material, such as a shellfish 25, the electrolyte may be a salt-bearing liquid, such as sea water. Normally, many items for treatment are present at one time; only one has been shown in FIG. 9 for sake of clarity.

The electrodes are formed of materials that are inert to the electrolytes and to the host materials to be processed. One such material is carbon, which may have a "U" channel edge contact of stainless steel, to which connecting wires are attached. Other successful electrode materials include stainless steel, tantalum and titanium.

The host material to be treated may be handled in batch lots in rectangular baskets. Such baskets, for best results, should be non-conductive except for the two sides parallel to the treatment cell electrodes, which sides should be electrically conductive.

Alternatively, a slow flow-through hydraulic arrangement may be used, in which the material is incoming at one end of the cell and outgoing at the other.

A preferred embodiment of a treatment cell for three-phase apparatus is shown in FIG. 10. Part of the outer container enclosure 27 has been broken away to show the inner construction, and the forward end is sectional for the same purpose.

The objective in a three-phase cell is to arrange three electrodes in a symmetrical configuration, such that the electrical flux charges between the electrodes are substantially uniform over the working areas. All electrode faces contacting the electrolyte must be parallel, of equal surface areas and equidistant at all points to assure uniform current flow at all points within the chamber.

In FIG. 10, segmented electrodes 28, 29 and 30 occupy much of the volume of outer container 27. This allows parallel electrode surfaces to be presented from one electrode to the other. This is typically a flow-through embodiment. The electrolyte and the material treated are flowed through each of the three channels, as indicated by the arrows in the channel revealed by the break-away portion of the container.

The electrodes are composed of the same or similar materials to those used in the single phase apparatus described above.

Central cylindrical surface 31 is of electrically insulating material, such as a plastic or glazed refractory material. This prevents a flow of electrolyte in the central area between the electrodes where the flux charges would be other than that found between the parallel electrode faces resulting in non-uniform current densities.

FIG. 11 shows a three-phase schematic electrical circuit. Therein, entity 35 accepts conventional three-phase, or polyphase, power and transforms it to a higher or lower voltage as required to obtain effective energization of treatment cell 27. Both delta and "Y" connected windings are shown in entity 35 in a generic showing of a transformer. Either mode of connecting the windings may be used.

The output of entity 35 passes through three conductors into control circuitry 36. This is comprised of three separate single-phase control circuits, such as are shown in FIGS. 1, 3, 5 or 7. These separate circuits are controlled in concert so that each of the three phases is regulated in the same manner.

The output of control circuitry 36 is individually connected to electrodes 28, 29 and 30 of the three-phase treatment cell 27, for the electrical energization thereof.

The circuits, apparatus and operating parameters of this invention "electrocute" the unwanted organisms. Bacteria are not "exploded," contra to the prior art. The effect is not derrived from a cooking or pasteurization process. Importantly, the cellular structure of the host material is not altered due to the flow of current. This has been confirmed by optical microscopy.

It will be understood that a significant alteration in cellular structure is undesirable in the value of the host material as a comestible.

Numerous substances may be treated, among which are shellfish, fish, fruits, vegetables, fowl and meats.

The chief advantage of treatment is to reduce the bacterial or other organism count in the host material, thereby to prolong the time before spoilage sets in, and the time prior thereto during which flavorful taste is retained. Very significant reductions in bacterial count by this processing have been realized.

The preferred modes of processing were evolved as indicated by the successive schematic diagram figures herein.

First was phase control. When it became apparent that by increasing the conductivity of the electrolyte, thereby shortening the necessary duration of the conduction periods, the sterilization effect was greatly enchanced, a next step evolved.

This next step was pulse discharge. With sufficinet capacitance in the two storage capacitors plus a pulse forming network there was a very significant killing effect on the bacterial population and very little thermal rise.

A third step embraced pulse discharge followed by a conduction angle, as 22 and 9' in FIG. 8. This gives maximum sterilization effect at minimum heating of the material.

The following data was obtained with the invention and its various embodiments without permitting the treated materials to rise in temperature above 25 degrees Celcius:

Utilizing the embodiment of FIG. 1, the results for shrimp were:
Control sample: 1,600,000 bacteria per gram
Average of treated samples: 201,250 bacteria per gram
(Bacterlogical tests by independent laboratory.)
Utilizing the embodiment of FIG. 3, the results for shrimp were:
Control sample: 2,000,000 bacteria per gram
Average of treated samples: 150,000 bacteria per gram
(Bacterlogical tests by independent laboratory.)
Utilizing the embodiment of FIG. 5, the results for shrimp were:
Control sample: 350,000,000 bacteria per gram
Average of treated samples: 320,000 bacteria per gram
Utilizing the embodiment of FIG. 7, the results for scallops were:
Control sample: 40,000 bacteria per gram
Average of treated samples: At or below the lower limit of
laboratory testing resolution.

It is possible to establish a treatment procedure for each substance to be treated. This is based on the substance treated, its initial condition, the degree of sterilization desired, and the parameters of the apparatus used. The latter includes the circuit used and the configuration of the treatment cell. It is unlikely that the treatment procedure needs to varied during a processing run with a given host material.

The invention is effective in treating materials containing pathogenic multicellular organisms. In certain raw fish, for example, there can exist such organisms, which, when consumed by humans are quite harmful. One is diobothriocephalus latus, a worm found in white fish. Another is tricini infested pork, which causes trichinosis in humans.

Usual tap water may be used as an alternate to sea water as an electrolyte. The conductivity of tap water can be increased if required, by the addition of certain quantities of ionizable chemical salts or even acid or base chemicals.

For maximum efficiency the electrolyte has slightly less conductivity than does the host material being treated. This causes the current to concentrate to a nominal degree through the host material.

In applying the invention, the greater the peak amplitude of the current the shorter is the processing time and the lesser is the power dissipated in the media and electrolyte.

If a reduced degree of sterilization is desired, this is obtained by a shorter processing time or reduced amplitude of the current.

As to the voltage, the greater the separation of the electrodes and/or the lower is the conductivity of the electrolyte, the more voltage is required to obtain a given flow of current.

The term "organism" is generic as used herein. It includes bacteria, yeasts, viri, parasitic worms, insect lavra and eggs, and spores of micro-organisms. By and large, any living organism within the host material is subjected to the current pulses and is electrocuted. These living organisms include the range from micro-organisms to macro-organisms.

Inherent in this invention is the concept of phase control; that is, passing a current pulse through the host medium for only a brief period of each half cycle of incoming alternating current. This is as shown in FIG. 2. The employment of a pulse forming network 33 causes $dI/dt$ through the media being treated to be substantially greater than if no such network were used thereby resulting in increased efficacy of the invention and hence the ability to obtain low organism counts with little temperature rise.

Adding pulse dischrages from capacitors, as 12 and 14 of FIG. 3, enhances the killing effect of the process upon the unwanted organisms while further reducing the power dissipation. Note FIG. 4.

It has been found that a combination of the two current waveforms gave a killing effect superior to either of them alone. This is accomplished by the apparatus of FIG. 5 and is illustrated by the waveforms of FIG. 6, having portions 21 and 9'. Where greater killing effect is required the apparatus of FIG. 7 and the waveform of FIG. 8 is used. The current spike 22 is of greater amplitude than in FIG. 6.

I claim:

1. Apparatus for killing organisms resident within a host, comprising:
   (a) an electrically non-conductive container (2 or 27) for receiving the host,
   (b) an electrically conductive liquid (24) within said container and surrounding the host,
   (c) electrodes (3,4 or 28,29,30) symmetrically disposed within said container, characterized by each electrode face having equal surface area and being parallel to and equidistant at all points from its next adjacent electrode, and contacting said liquid, and
   (d) a pulsed electric source (1,3,5,6,13, etc.) connected to said electrodes to pass electric current through the liquid, the host, and concomitantly through the organisms, in the form of short pulses having a duration within the range of 200 microseconds to five milliseconds each, of successive alternate polarity and a rise time of a small fraction of the 200 microsecond interval, and not of less than 50 milliamperes average current per square centimeter of host, ranging up to five amperes per square centimeter, and occurring between 100 and 1,000 times per second.

2. The apparatus of claim 1, in which;
   (a) the electrically conductive liquid is tap water.

3. The apparatus of claim 1, in which;
   (a) the electrically conductive liquid is tap water with salts, acids or base chemicals added thereto.

4. The apparatus of claim 1, in which;
   (a) the electrically conductive liquid is sea water.

5. The apparatus of claim 1, in which;
   (a) said electrodes are of equal surface areas, parallel and equidistant from eachother at all points in contact with the electrolyte liquid.

6. The apparatus of claim 1, in which said pulsed electric source comprises;
   (a) a source of alternating current power (1);
   (b) a pair of thyristors (5, 6) oppositely poled and connected to said source of alternating current power;
   (c) an electrical connection from both of said thyristors to one said electrode (3);
   (d) an electrical connection from the other said electrode (4) to said source of alternating current power; and
   (e) an oscillatory trigger means (13) connected to each of said thyristors (5, 6), to trigger each thyristor into conduction near the end of each half-cycle of current from said source of alternating current power (1).

7. The apparatus of claim 1, in which said pulsed electric current source comprises;
   (a) a source of alternating current power (1);
   (b) a pair of thyristors (5, 6), oppositely poled, connected to said source of alternating current power through like poled diodes (18, 19); and
   (c) a pair of capacitors (12', 14'), connected to said thyristors to accumulate oppositely poled electric charges, and also connected to said electrodes (3, 4) through said thyristors to pass said current pulses through said host and said organisms.

8. The apparatus of claim 1, in which said pulsed electric source comprises;
   (a) a pair of oppositely poled direct current power supplies (10, 11);
   (b) a capacitor (12, 14) separately connected across each said direct current power supply;
   (c) oppositely poled thyristors (5, 6) connected to said capacitors and to one of said electrodes; and
   (d) a return connection (20) from the other said electrode (4) to said direct current power supplies.

9. The apparatus of claim 8, which additionally includes;
   (a) a diode (18, 19) connected to each of said oppositely poled thyristors, in the same polarity as that of said thyristors; and
   (b) a source of alternating current power (1) connected to both of said diodes and to said return connection.

10. The apparatus of claim 1, in which said pulsed electric source includes;
    (a) a pulse-forming netwrok (33) interposed between the source (5, 6, etc.) and electrode (3) to enhance the rate of change of current with respect to time (dI/dt) of the pulses of said source.

11. The apparatus of claim 1, in which said container comprises;
    (a) an outer cylindrical enclosure (27);
    (b) plural equally extensive, parallel and equally spaced apart electrodes (28, 29, 30), coextensive within said enclosure; and
    (c) a connection from each of said plural electrodes to a phase of a pulsed electric source (35, 36) having plural phases.

12. The apparatus of claim 1, in which said pulsed electric source comprises;
    (a) a plural phase source of alternating current electrical energy (35);
    (b) plural control circuits (36) individually connected to a phase of said plural phase source; and
    (c) a connection from each of said plural control circuits to a separate electrode of a container (27) having plural electrodes (28, 29, 30).

* * * * *